US007585313B2

(12) United States Patent
Kwak et al.

(10) Patent No.: US 7,585,313 B2

(45) Date of Patent: Sep. 8, 2009

(54) ROTATABLE INTERSPINOUS SPACER

(75) Inventors: Seungkyu Daniel Kwak, Grafton, MA (US); John Riley Hawkins, Cumberland, RI (US)

(73) Assignee: DePuy Spine, Inc., Raynham, MA (US)

(*) Notice: Subject to any disclaimer, the term of this patent is extended or adjusted under 35 U.S.C. 154(b) by 477 days.

(21) Appl. No.: 11/315,660

(22) Filed: Dec. 22, 2005

(65) Prior Publication Data

US 2007/0161992 A1 Jul. 12, 2007

(51) Int. Cl.
*A61B 17/70* (2006.01)
*A61F 2/30* (2006.01)

(52) U.S. Cl. .................................... 606/249; 606/902

(58) Field of Classification Search ................. 606/248, 606/249, 902, 246

See application file for complete search history.

(56) References Cited

U.S. PATENT DOCUMENTS

| | | | | |
|---|---|---|---|---|
| 4,759,769 | A | 7/1988 | Hedman | |
| 5,071,437 | A | 12/1991 | Steffee | |
| 5,401,269 | A | 3/1995 | Buttner-Janz | |
| 5,527,312 | A | 6/1996 | Ray | |
| 5,645,599 | A | 7/1997 | Samani | |
| 5,824,093 | A | 10/1998 | Ray | |
| 5,824,094 | A | 10/1998 | Serhan | |
| 6,001,130 | A | 12/1999 | Bryan | |
| 6,068,630 | A | 5/2000 | Zuchermann | |
| 6,113,637 | A | 9/2000 | Gill | |
| 6,610,089 | B1 | 8/2003 | Liu et al. | |
| 6,949,123 | B2 * | 9/2005 | Reiley | 623/17.11 |
| 2004/0220568 | A1 * | 11/2004 | Zucherman et al. | 606/61 |
| 2005/0261768 | A1 | 11/2005 | Trieu | |
| 2007/0032790 | A1 * | 2/2007 | Aschmann et al. | 606/61 |
| 2007/0233076 | A1 * | 10/2007 | Trieu | 606/61 |
| 2008/0027438 | A1 * | 1/2008 | Abdou | 606/61 |
| 2008/0045958 | A1 * | 2/2008 | Zucherman et al. | 606/61 |

FOREIGN PATENT DOCUMENTS

| | | | | |
|---|---|---|---|---|
| EP | 1201197 | A1 | * | 5/2002 |
| WO | WO 03015645 | A1 | * | 2/2003 |
| WO | WO 2007012940 | A1 | * | 2/2007 |

* cited by examiner

*Primary Examiner*—Eduardo C Robert
*Assistant Examiner*—Ellen Rust
(74) *Attorney, Agent, or Firm*—Thomas M. DiMauro

(57) ABSTRACT

An interspinous spacer having opposed, pivotally connected s-shaped members that can enter the interspinous space in an initial state and then rotate to a final state to secure the implant to the adjacent interspinous processes.

20 Claims, 11 Drawing Sheets

325
328
351
326
341
329

ROTATABLE INTERSPINOUS SPACER

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or folding of the ligamentum flavum may further compress and extend into the spinal canal. This condition, called "spinal stenosis", narrows the spinal canal and causes impingement of tissue upon the spinal cord, thereby producing pain.

There have been numerous attempts to provide relief for these afflictions by providing a spacer that inserts between adjacent spinous processes present in the posterior portion of the spinal column. This spacer essentially lifts the upper spinous process off of the lower spinous process, thereby relieving stenosis. In general, these interspinous implants are adapted to allow flexion movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zucherman discloses a plurality of implants having a body portion and lateral wings. The body portion is adapted to seat between the adjacent spinous processes, while the wings are adapted to prevent lateral movement of the body portion, thereby holding it in place between the adjacent spinous processes. The designs disclosed in FIGS. 15, 80 and 84 of Zuchermann comprise central body having an integral wing.

Although the Zuchermann device achieves spinal distraction, it nonetheless possesses some limitations. First, since the Zuchermann central bodies have at least one integral wing, the clinician may encounter difficulty in sizing the central body independently of delivering the lateral wings. Second, the expansive geometry of the disclosed devices may not lend itself to minimally invasive surgical techniques seeking to conserve muscle mass and soft tissue in the regions adjacent the spinous processes.

U.S. Pat. No. 5,645,599 ("Samani") attempts to relieve spinal stenosis by essentially inserting a flexible horseshoe-shaped device between the adjacent spinous processes. Although the Samani device desirably provides a self-limiting flexibility, it nonetheless suffers from some inadequacies. For example, the Samani device does not provide for natural physiologic rotational movement, nor for post-operative adjustment. In addition, the Samani device discloses the insertion of a bearing cushion, and the adhesive bonding of the bearing cushion to the horseshoe element. However, it is believed that mere adhesive bonding of these elements would cause the cushion to be prone to migration.

SUMMARY OF THE INVENTION

The present invention relates to an expandable interspinous spacer that can be laterally inserted between adjacent spinous processes in an initial state, and then one portion of the device is pivotally rotated relative to a second portion of the device to provide firm securement to the adjacent spinous processes.

In a preferred embodiment, the spacer comprises two S-shaped members that can pivot about a pair of central elements. Because the S-shaped members are oriented in opposite directions, the spacer has a narrow distal portion in its initial state that allows for its minimally invasive insertion between the adjacent spinous processes. Once this distal portion is positioned substantially on the distal side of the interspinous space, the S-shaped members are rotated past each other in opposite directions about the central element to a final state. As the S-shaped members rotate, the spacer pulls itself into the interspinous space, thereby positioning the central element within the interspinous space. Once in this final position, the two bodies are locked together.

Therefore, in accordance with the present invention, there is provided an interspinous implant for insertion between adjacent spinous processes, the implant comprising:

a) a first S-shaped member having a central element, an upper arm attached to the central element and adapted to bear against the upper spinous process, and a lower arm attached to the central element and adapted to bear against the lower spinous process, and b) a second S-shaped member having a central element, an upper arm attached to the central element and adapted to bear against the upper spinous process, and a lower arm attached to the central element and adapted to bear against the lower spinous process, wherein the central elements of the first and second members are pivotally connected.

DETAILED DESCRIPTION OF THE INVENTION

For the purposes of the present invention, the term "interspinous" refers to the volume located between two adjacent spinous processes of adjacent vertebrae. The terms "anterior" and "posterior" are used as they are normally used in spinal anatomy. Accordingly, the "anterior" portion of the interspinous device is that portion rests relatively close to the spinal cord, while the "posterior" portion of the interspinous device is that portion rests relatively close to the skin on the patient's back. Now referring to FIG. 7C, there is provided an anatomic "functional spinal unit" or FSU comprising an upper vertebrae having an upper vertebral body $VB_U$ and an upper spinous process $SP_u$, a lower vertebra having a lower vertebral body $VB_L$ having a lower spinous process $SP_L$. The vertebral bodies lie in the anterior A portion of the FSU, while the spinous processes lie in the posterior portion P of the FSU. Disposed between the vertebral bodies is a disc space "disc". Disposed between the spinous process is an "interspinous region".

Figure 1:
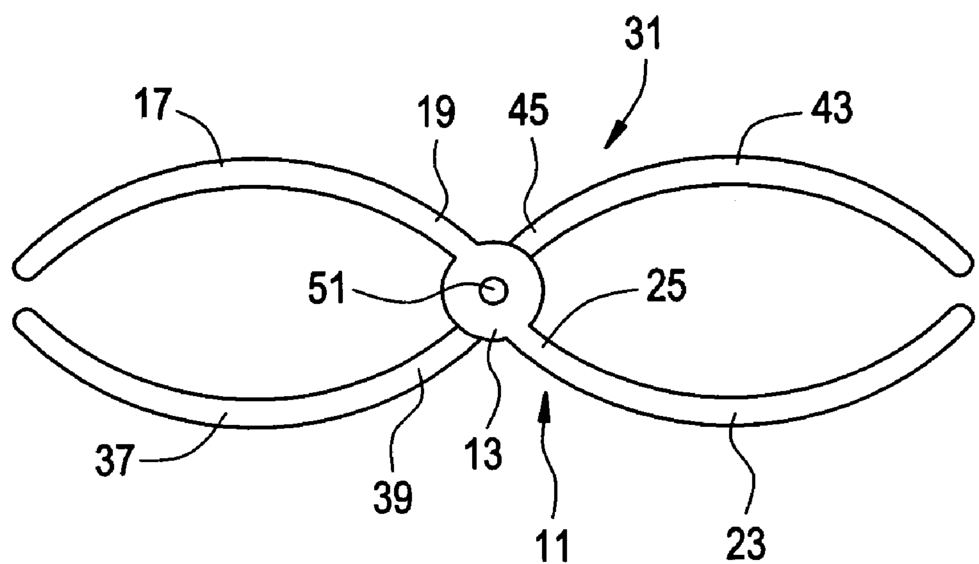
FIG. 1 is a top view of a first embodiment of an interspinous spacer of the present invention in its initial state.

Now referring to FIG. 1, there is provided an interspinous implant for insertion between adjacent spinous processes. The implant in its initial state comprises:

a) a first S-shaped member 11 having a central element 13 having a throughbore, a distal concave arm 17 having a proximal end 19 attached to the central element and a proximal concave arm 23 having a distal end 25 attached to the central element, wherein the concave arms face away from each other, and b) a second S-shaped member 31 having a central element having a throughbore, a distal concave arm 37 having a proximal end 39 attached to the central element and a proximal concave arm 43 having a distal end 45 attached to the central element, wherein the concave arms face away from each other, wherein the central elements of the first and second members are pivotally connected by a pivot pin 51 that extends through the throughbores of the central elements.

Also as shown in FIG. 1, in the initial state, the proximal concave arm of the first S-shaped member opposes the proximal concave arm of the second S-shaped member, while similarly the distal concave arm the first S-shaped member opposes the distal concave arm of the second S-shaped member.

Figure 2:
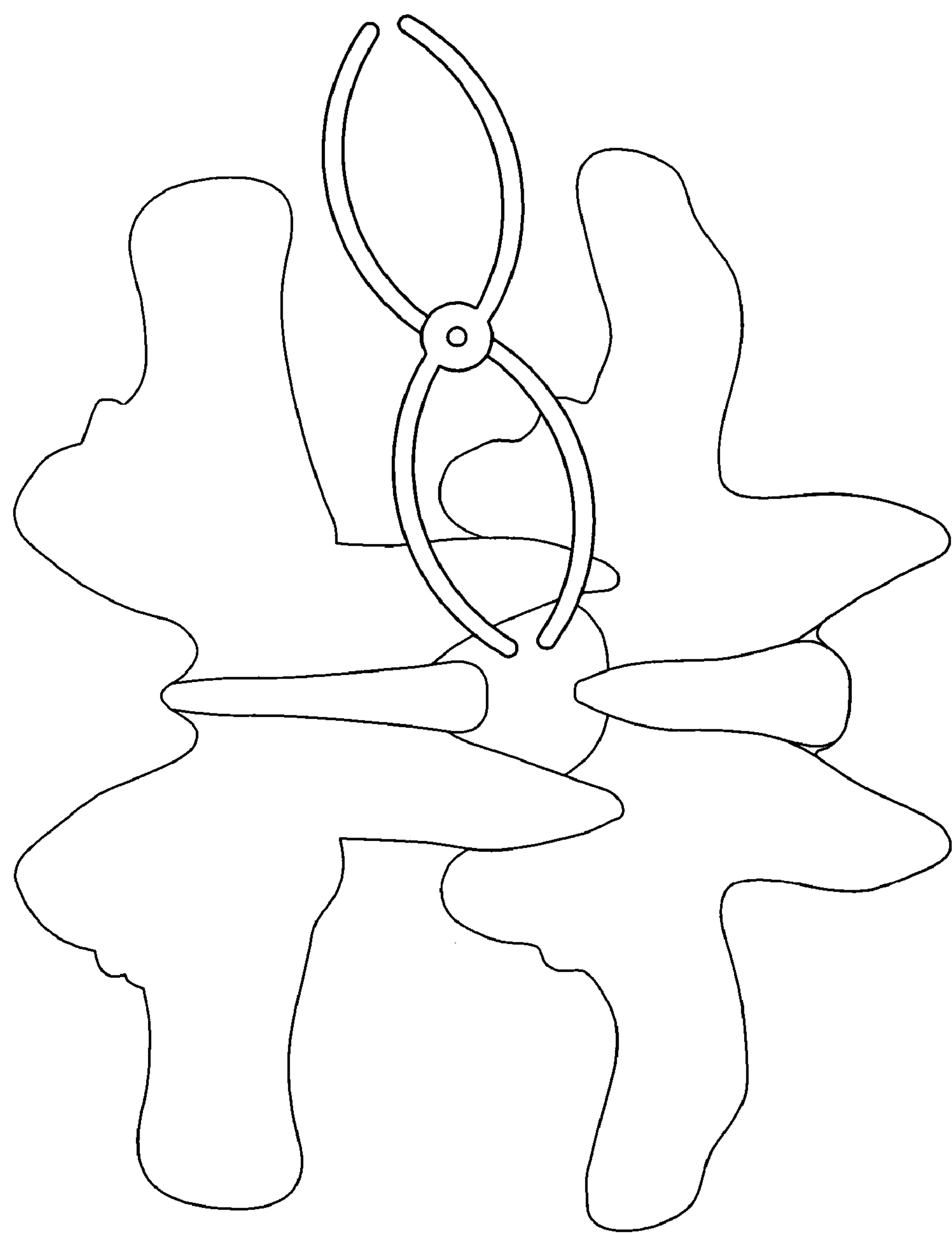
FIG. 2 is a posterior view of the interspinous spacer of FIG. 1 being inserted laterally between adjacent spinous processes so that the distal elements are positioned substantially on the distal side of the interspinous space, while the central element is positioned on the proximal side of the interspinous space.

Now referring to FIG. 2, the distal arms of the spacer are inserted between adjacent spinous processes so that these arms will become positioned substantially on the distal (left) side of the interspinous space, while the central element is positioned on the proximal (right) side of the interspinous space.

Figure 3:
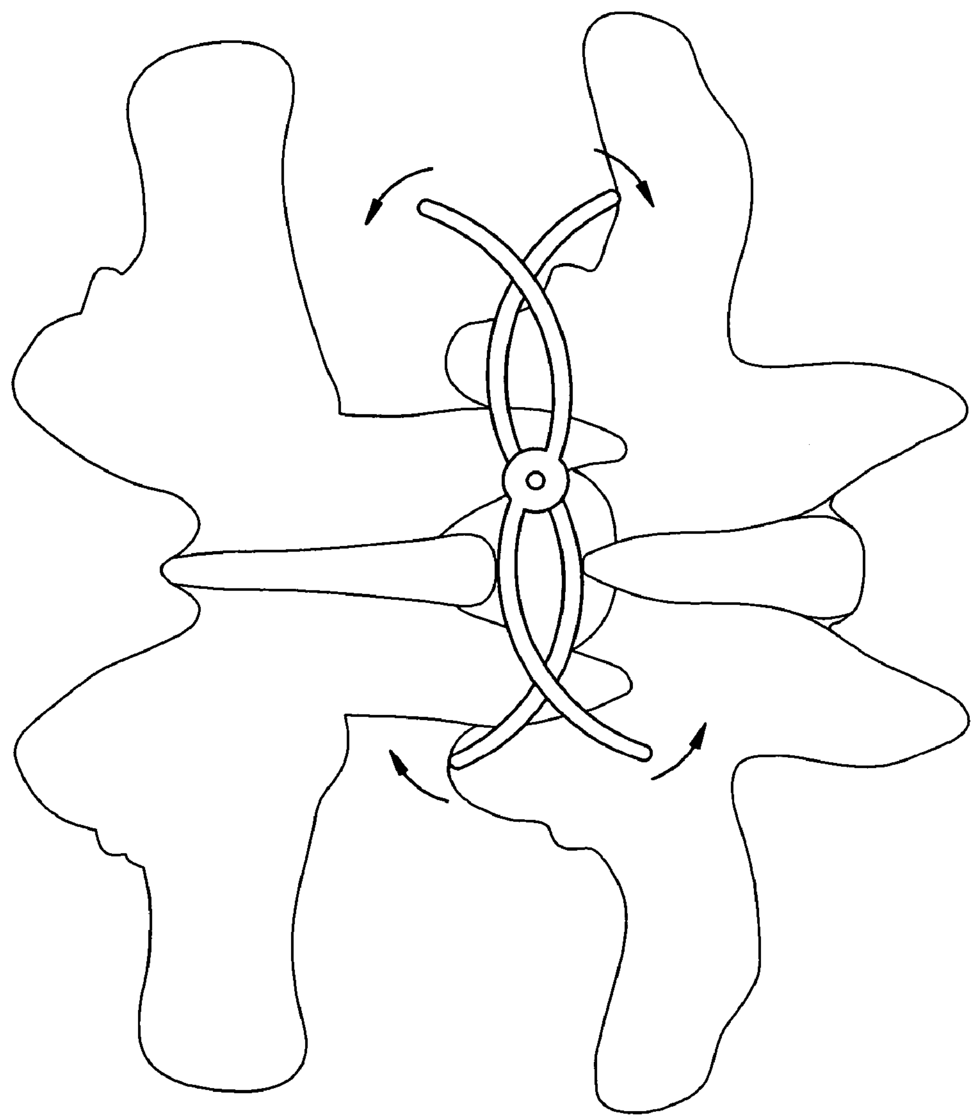
FIG. 3 is a posterior view of the interspinous spacer of FIG. 2 wherein, after its lateral insertion into the interspinous space, the S-shaped members are rotated past each other in opposite directions about the central element to its final state.

Now referring to FIG. 3, once these distal arms are positioned substantially on the distal (left) side of the interspinous space, these arms are rotated past each other in opposite directions about the central elements to bring the spacer to its final state.

Figure 4:
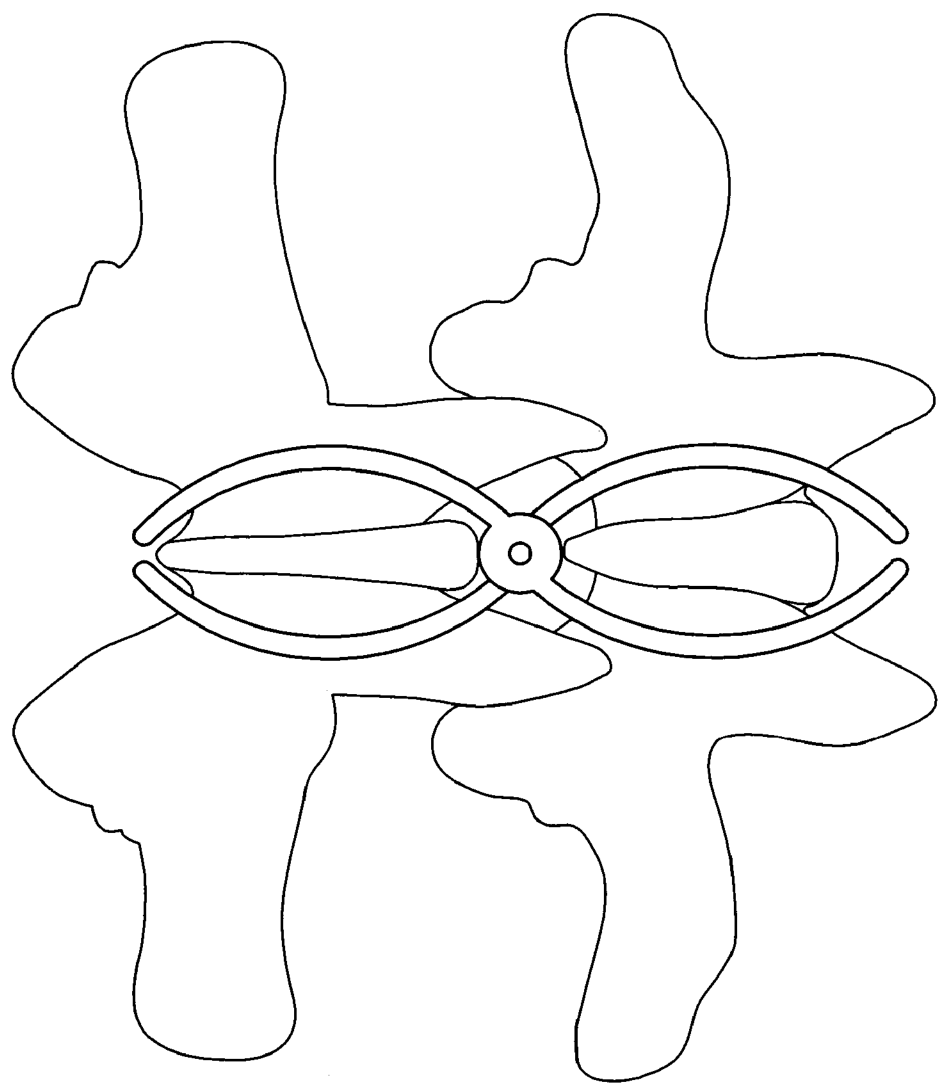
FIG. 4 is a posterior view of the interspinous spacer in its final state and centrally positioned within the interspinous space.

Now referring to FIG. 4, as the S-shaped members rotate, the bearing of the distal arms upon the adjacent spinous processes acts to pull the rest of the itself into the interspinous space, thereby positioning the central elements within the interspinous space. Once in this final position, the two S-shaped members are locked together.

Therefore, in accordance with the present invention, there is provided a method of inserting an interspinous implant comprising the steps of:

a) providing an interspinous implant comprising:
   i) a first member having a central element, a distal concave arm having a proximal end attached to the central element and a distal end, and
   ii) a second member having a central element, a distal concave arm having a proximal end attached to the central element and a distal end, wherein the distal concave arms substantially oppose each other, and wherein the central elements of the first and second members are pivotally connected, b) inserting the distal concave arms between adjacent spinous processes so that the distal concave arms are positioned substantially on the distal side of the interspinous space, and c) pivoting the distal end of the first member about the central element so that the distal concave arms pass from each other.

Figure 5A:
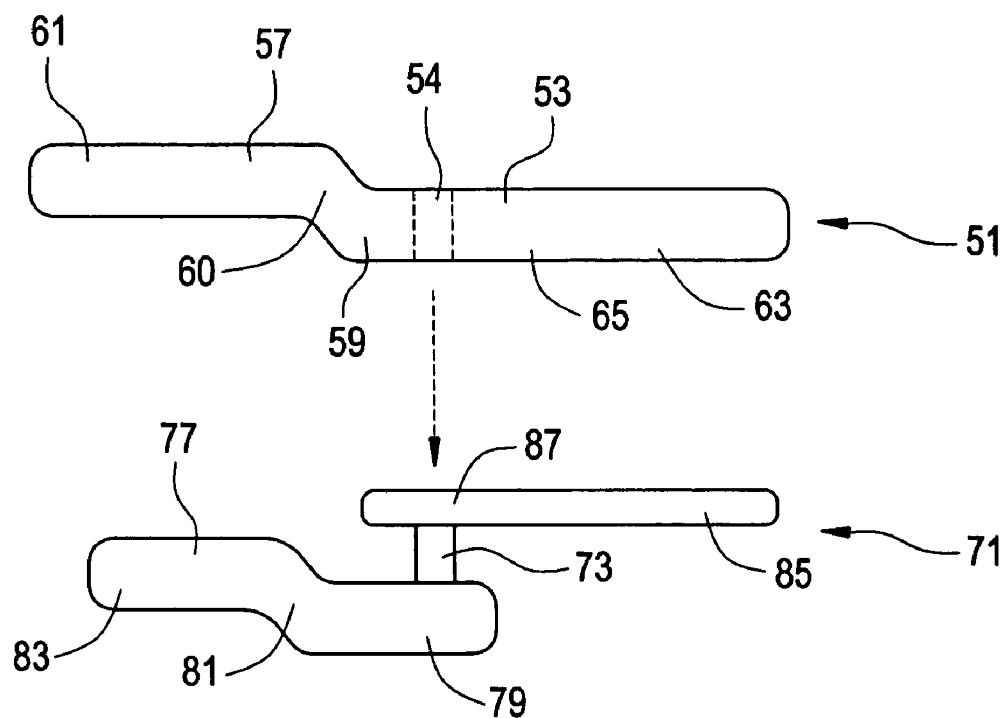
FIGS. 5A-5B disclose exploded and assembled side views of a second embodiments of the present invention in its initial state, wherein the concave arms traverse several planes.
Figure 5B:
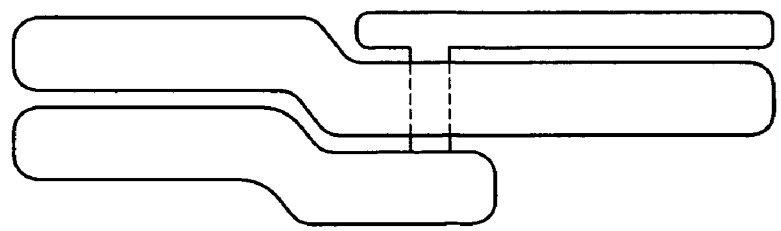

Now referring to FIGS. 5A and 5B, there is provided an interspinous implant 50 for insertion between adjacent spinous processes. The implant is in its initial state and comprises:

a) a first S-shaped member 51 having:
   i) a central region 53 having a throughbore 54,
   ii) a distal concave arm 57 having a proximal end 59 lying in a first plane and attached to the central element, an intermediate curved region 60 and a distal end 61 lying in a second plane, and
   iii) a proximal concave arm 63 lying in the first plane and having a distal end 65 attached to the central element, wherein the concave arms of the first S-shape member face away from each other, and b) a second S-shaped member 71 having:
   i) a central element 73 located in the first plane,
   ii) a distal concave arm 77 having a proximal end 79 lying in a third plane and attached to the central element, an intermediate curved region 81 and a distal end 83 lying in the first plane,
   iii) a proximal concave arm 85 lying in the second plane and having a distal end 87 attached to the central element, wherein the concave arms of the second S-shape member face away from each other, and wherein the first and second S-shaped members are pivotally connected by the central element 73 that extends through the throughbore 54 of the central region.

In an alternative embodiment, the central element 73 of the second S-shaped member is an independent component, and the distal and proximal arms of the second S-shaped member have throughbores that accommodate the central element.

Figure 6A:
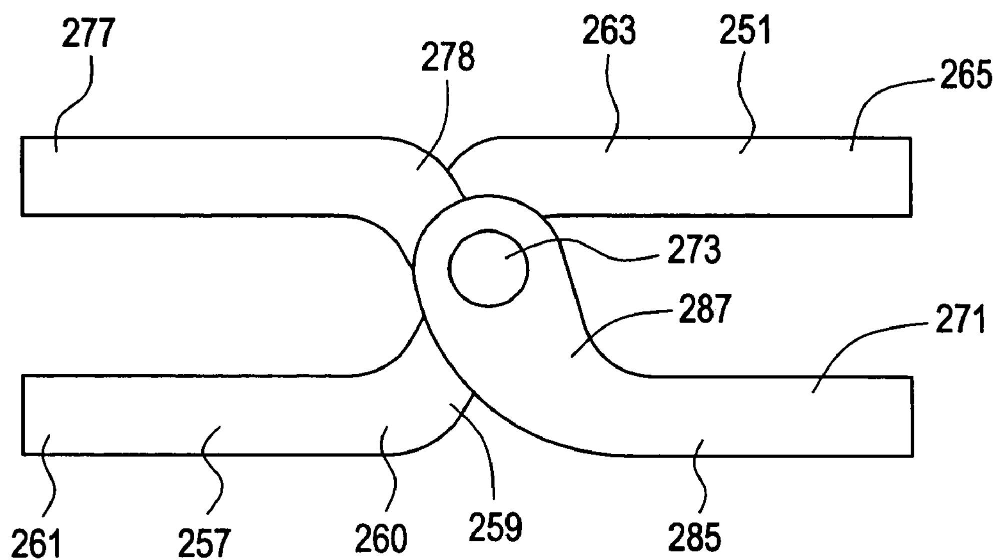
FIGS. 6A-6B disclose upper and side views of a second embodiment of the present invention in its final state.
Figure 6B:
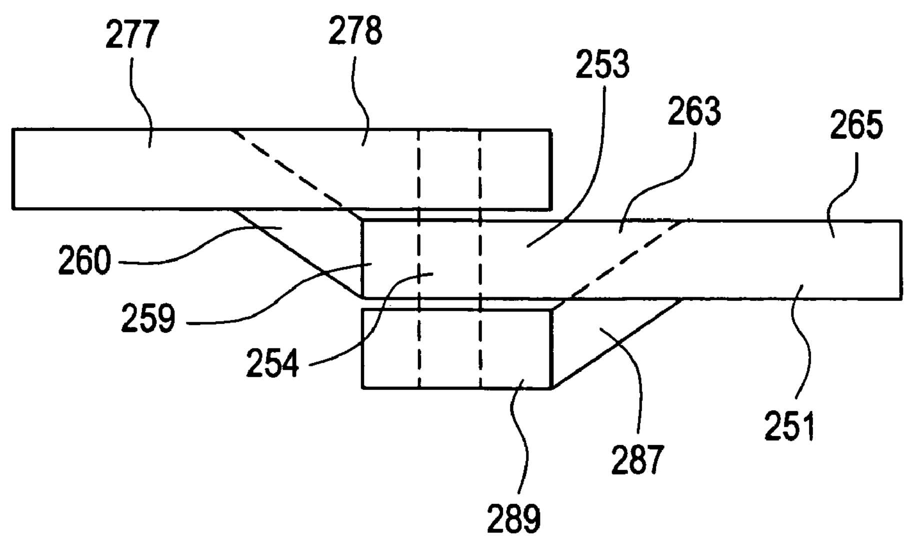

Now referring to FIGS. 6A and 6B, there is provided an interspinous implant 50 for insertion between adjacent spinous processes. The implant is in its final state and comprises:

c) a first S-shaped member 251 having:
   i) a central region 253 having a throughbore 254,
   ii) a distal concave arm 257 having a proximal end 259 lying in a first plane and attached to the central element, an intermediate curved region 260 and a distal end 261 lying in a second plane, and
   iii) a proximal concave arm 263 lying in the first plane and having a distal end 265 attached to the central element, wherein the concave arms of the first s-shape member face away from each other, and d) a second S-shaped member 271 having;

i) a central element 273 located in the first plane, ii) a distal concave arm 277 lying in the second plane and having a proximal end 278 attached to the central element, iii) a proximal concave arm 285 having a distal end lying in the third plane and attached to the central element, an intermediate curved region 287, and a proximal end 289 lying in the first plane, wherein the concave arms of the second s-shape member face away from each other, and wherein the first and second S-shaped members are pivotally connected by the central element 273 that extends through the throughbore 254 of the central region.

The advantage of the design of FIGS. 6A and 6B is that, in its final state, the upper arms lie in the same plane and the lower arms lie in the same plane. That is, the distal concave arm of the first S-shaped member lies in a first plane and the proximal concave arm of the second S-shaped member lies in the first plane. Also, the proximal concave arm of the first S-shaped member lies in a second plane and the distal concave arm of the second S-shaped member lies in the second plane.

Figure 7A:
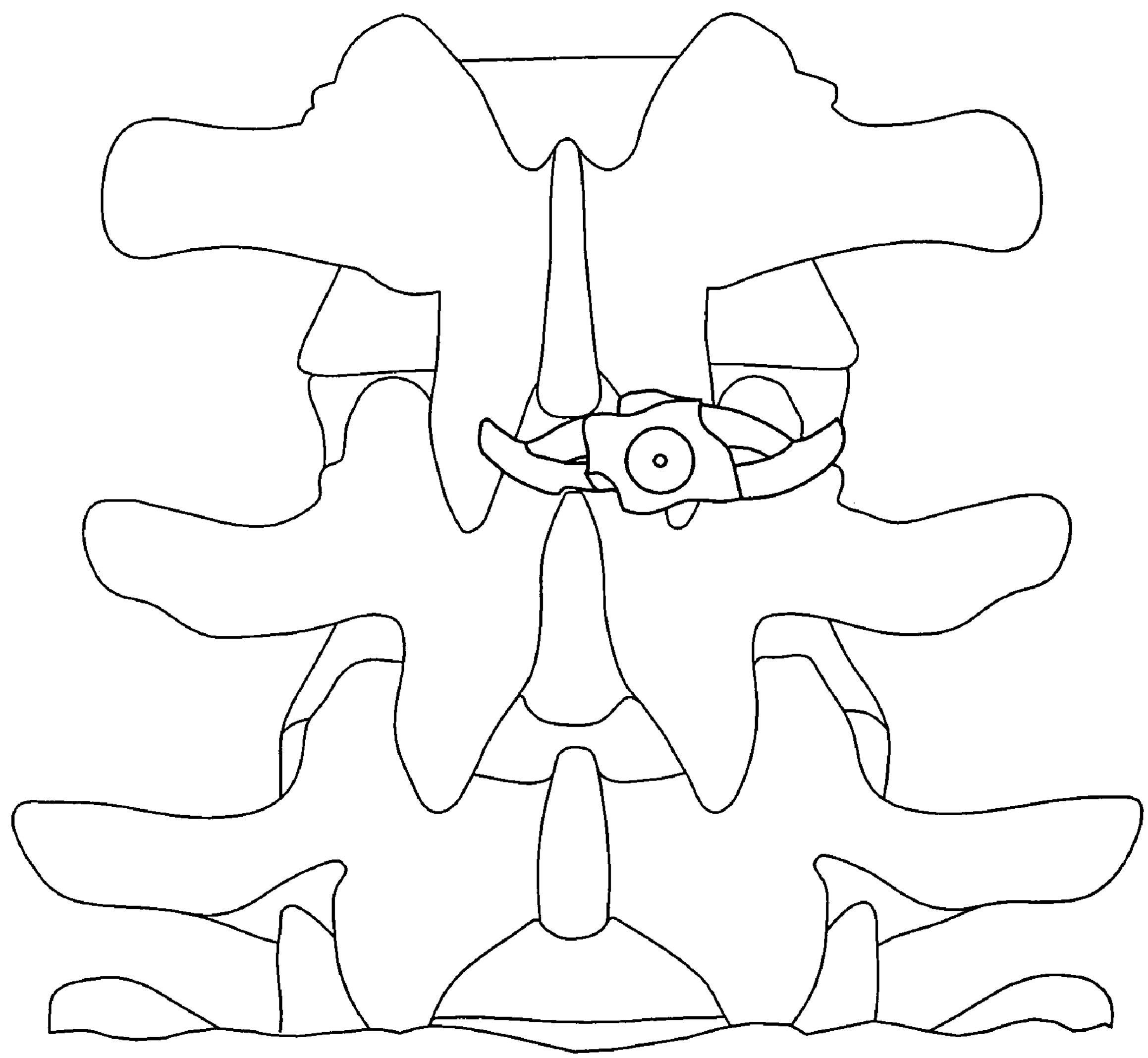
FIG. 7A is a posterior view of a second embodiment of the interspinous spacer of the present invention being inserted laterally in its initial state between adjacent spinous processes so that the distal elements are positioned partially on the distal (left) side of the interspinous space, while the central element is positioned on the proximal (right) side of the interspinous space.
Figure 7B:
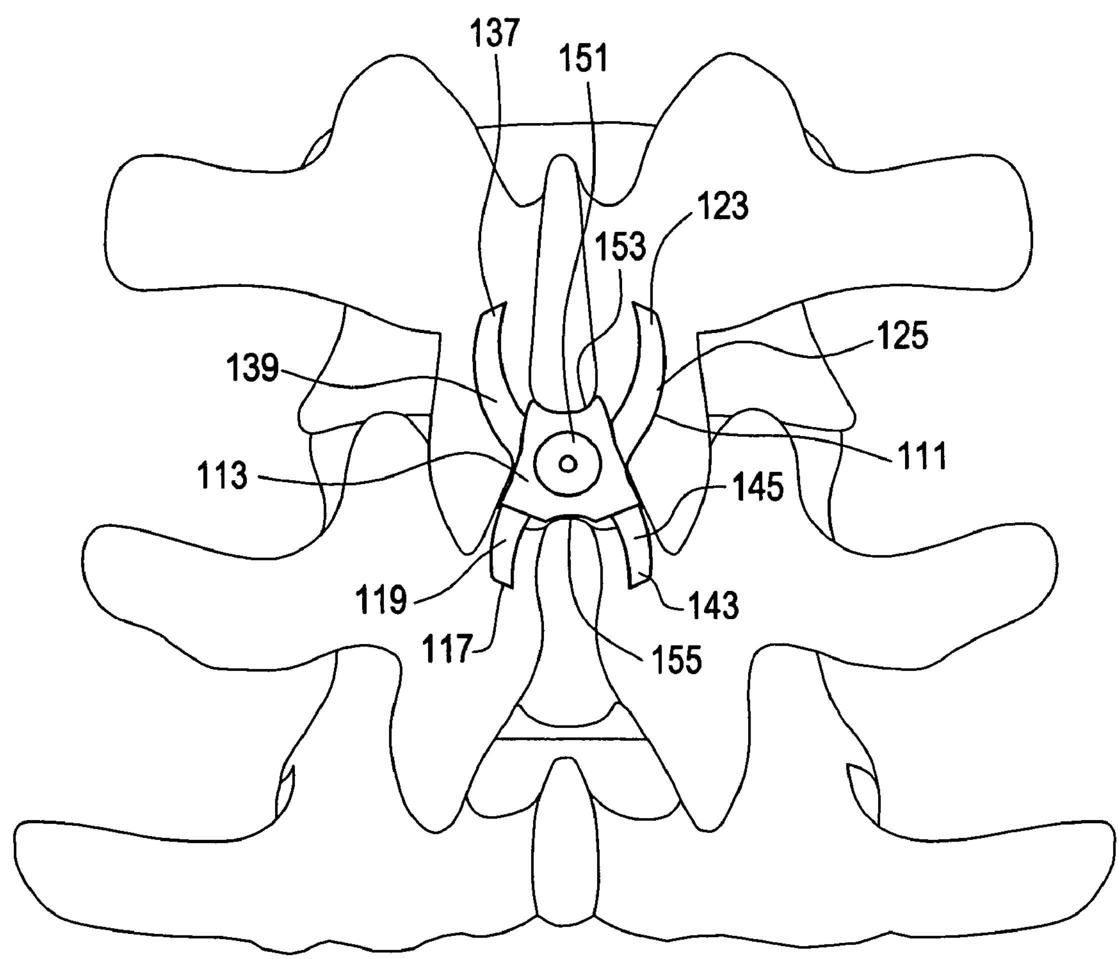
FIG. 7B is a posterior view of the interspinous spacer of FIG. 7A centrally positioned within the interspinous space in its final state.
Figure 7C:
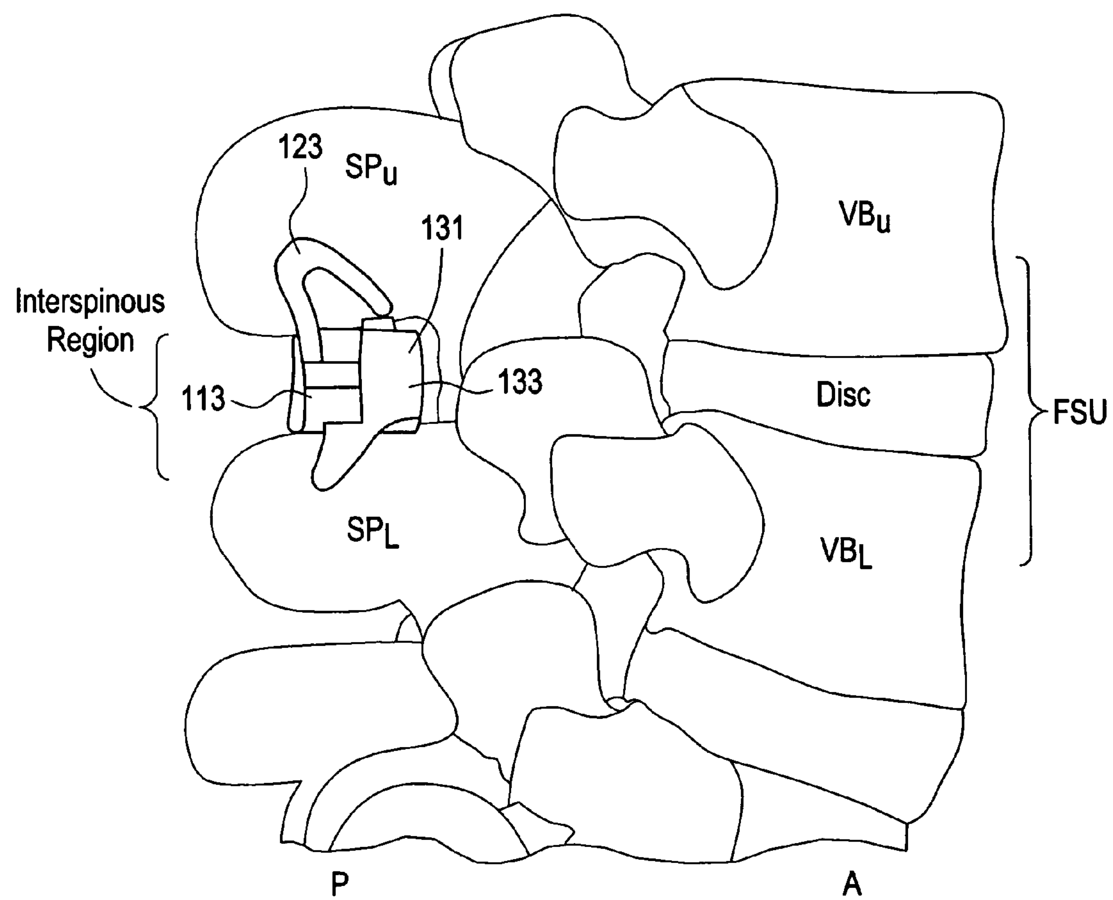
FIG. 7C is a side view of the interspinous spacer of FIG. 7B in its final state centrally positioned within the interspinous space.

Now referring to FIGS. 7A-C, there is provided a posterior view of an interspinous implant 101 being inserted between adjacent spinous processes. Referring to FIG. 7B, the implant comprises:

a) a first S-shaped member 111 having a central element 113, a distal concave arm 117 having a proximal end 119 attached to the central element and a proximal concave arm 123 having a distal end 125 attached to the central element, wherein the concave arms face away from each other, and b) a second S-shaped member 131 having a central element 133, a distal concave arm 137 having a proximal end 139 attached to the central element and a proximal concave arm 143 having a distal end 145 attached to the central element, wherein the concave arms face away from each other, wherein the central elements of the first and second members are pivotally connected by a pivot pin 151.

Also as shown in FIG. 7A, in this initial state, the proximal concave arm of the first S-shaped member opposes the proximal concave arm of the second S-shaped member, while similarly the distal concave arm the first S-shaped member opposes the distal concave arm of the second S-shaped member. In this FIG. 7A, the distal arms of the spacer are partially inserted between adjacent spinous processes so that these arms are positioned partially on the distal (left) side of the interspinous space, while the central element is positioned on the proximal (right) side of the interspinous space.

Now referring to FIG. 7B, once these distal arms are positioned substantially on the distal side of the interspinous space, the S-shaped members are rotated past each other in opposite directions about the central element to bring the spacer to its final state. The bearing of the distal arms upon the adjacent spinous processes acts to pull the rest of the itself into the interspinous space, thereby positioning the central element within the interspinous space. Once in this final position, the two S-shaped members are locked together.

Now referring to FIG. 7B, central element 113 contains concave bearing surfaces 153 and 155 for securing the implant to the upper and lower spinous processes. As seen in FIG. 7C, the extension of the concave arm in the anterior-posterior direction provides a holding feature 123 that allows for better securement of the device to the spinous process against which it bears.

In some embodiments, the central elements of the implant are joined together by a pin and groove arrangement. Now referring to FIGS. 8A-8B, in some embodiments, a first S-shaped member 324 has a projection 325 extending from an inner face 341 of the central element 326 thereof and a second S-shaped member 329 has a corresponding groove 327 extending into the inner face 343 of the central element 328 thereof. Preferably, the projection fits into the groove and may articulate in the groove to allow relative pivoting movement of the arms.

In some embodiments, the implant has a locking element. Preferably, the locking element comprises a pin having a leaf spring.

Figure 8A:
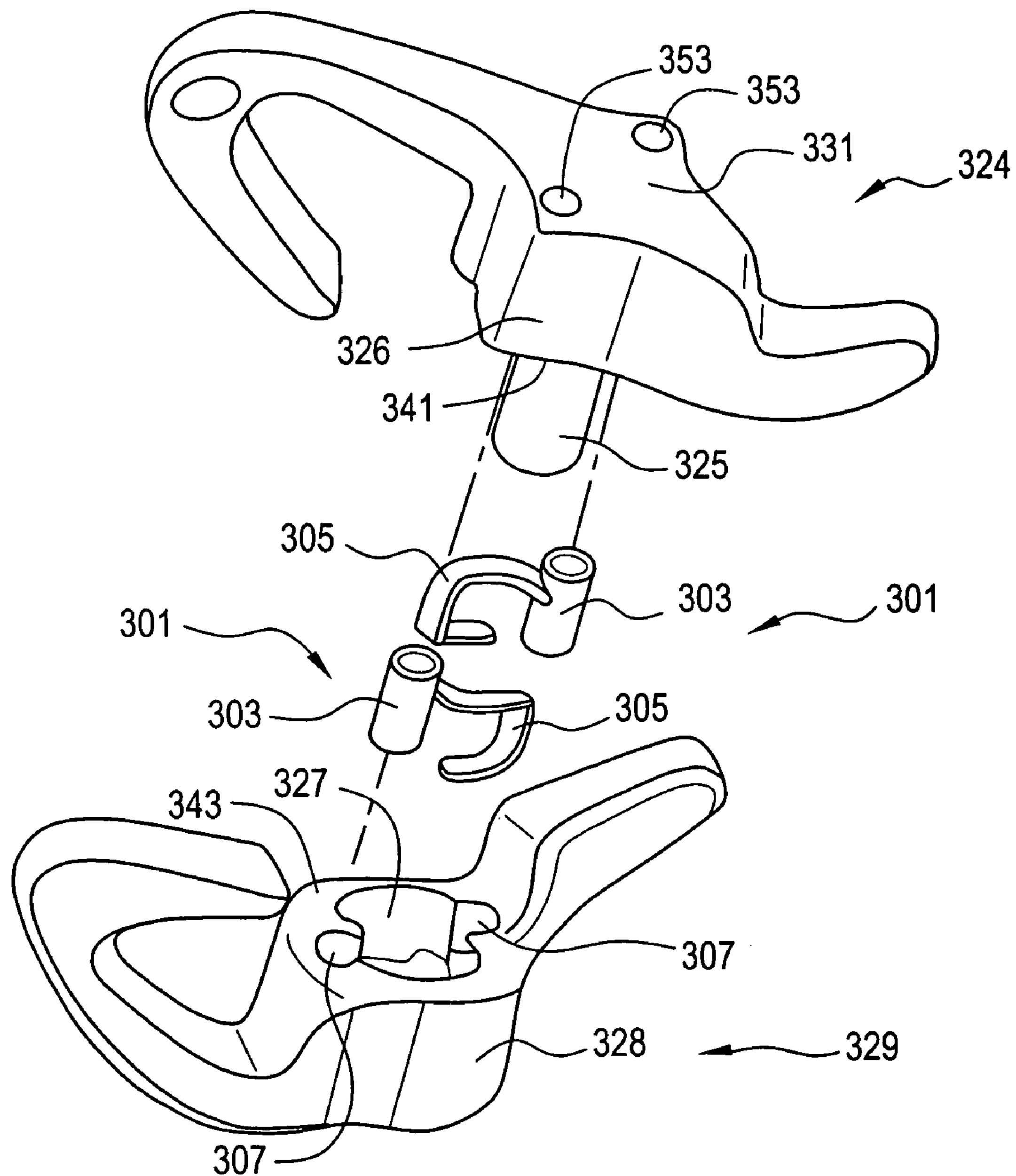
FIGS. 8A-8B disclose exploded and assembled views of an embodiment of the present invention having locking elements.
Figure 8B:
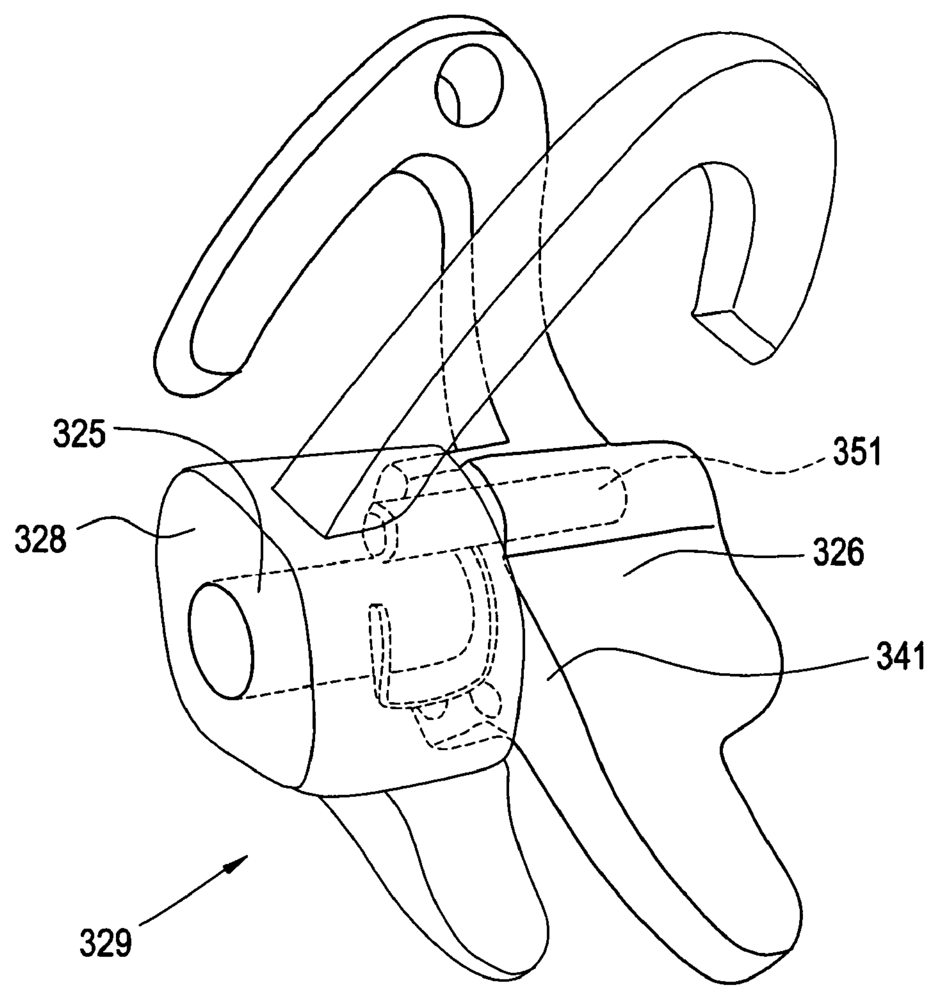

Now referring to FIGS. 8A-8B, in some embodiments, the device has a pair of locking elements. Each locking element 301 comprises a pin 303 having a leaf spring 305 extending therefrom. This locking element is received in the corresponding cavities 307 in each of the central elements. Central element 326 also has cavities 351 corresponding to the pins.

In use, when the device is in its initial position, the pins 303 with leaf springs initially sit completely in cavities 307 in central element 328. When the two S-shaped members are aligned in their final position, the cavities of the two central elements become aligned and the pin seated in the cavity 307 pops up to become partially seated in the opposing cavity on central element 326. This locks the implants in its final position. In some embodiments (such a during revision surgery), the leaf spring pins can be released by inserting a two-pronged key (not shown) in holes 353 on the outside face 331 of the first S-shaped member 324, and holding down the internal leaf spring pins while turning the key.

In some embodiments, the concave arms of the present invention are substantially U-shaped. In some embodiments, the concave arms of the present invention are substantially V-shaped.

In some embodiments (not shown), the central portion of the device is angled so that its anterior portion has a thickness that is greater than its posterior portion. This provides a desired angulation to the device. Preferably, each central element has an anterior portion having a thickness and a posterior portion having a thickness, and the thickness of each anterior portion is greater than the thickness of each posterior portion.

In preferred embodiments, the implant of the present invention is used posteriorly in conjunction with a motion disc inserted within the disc space of the anterior portion of the spinal column. For example, in some embodiments, the implant of the present invention is used in conjunction with a motion disc having a large range of motion ("ROM"). Various motion discs are described by Stefee et al. in U.S. Pat. No. 5,071,437; Gill et al. in U.S. Pat. No. 6,113,637; Bryan et al. in U.S. Pat. No. 6,001,130; Hedman et al. in U.S. Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference in their entireties. The flexibility of the flexible body provides resistance to extreme extension, thereby restricting the motion disc to a more narrow and more physiologically desirable range of motion.

Therefore, in accordance with the present invention, there is provided a kit for providing therapy to a functional spinal unit comprising an upper vertebrae having an upper spinous process, a lower vertebrae having a lower spinous process, and a disc space therebetween, the kit comprising:

a) an implant of the present invention, and b) an artificial intervertebral disc.

The implants disclosed herein may be suitably manufactured from any suitable biomaterial, including metals such as titanium alloys, chromium-cobalt alloys and stainless steel), ceramics (such as alumina and zirconia, and mixtures thereof) and polymers (such as PEEK, carbon fiber-polymer composites and UHMWPE). In preferred embodiments, the s-shaped members are made of titanium, titanium alloy, or PEEK.

We claim:

1. An interspinous implant for insertion between adjacent spinous processes, the implant comprising:

a) a first S-shaped member having a central element, a distal concave arm having a proximal end attached to the central element and a proximal concave arm having a distal end attached to the central element, wherein the concave arms face away from each other, and b) a second S-shaped member having a central element, a distal concave arm having a proximal end attached to the central element and a proximal concave arm having a distal end attached to the central element, wherein the concave arms face away from each other, and c) a pair of locking elements, each locking element comprising a pin having a leaf spring extending therefrom, wherein each locking element is received in a corresponding cavity in each of the central elements, wherein the central elements of the first and second members are pivotally connected.

2. The implant of claim 1 wherein, in an initial state, the proximal concave arm of the first S-shaped member opposes the proximal concave arm of the second S-shaped member.

3. The implant of claim 1 wherein, in an initial state, the distal concave arm the first S-shaped member opposes the distal concave arm of the second S-shaped member.

4. The implant of claim 1 wherein, in a final state, the distal concave arm of the first S-shaped member opposes the proximal concave arm of the second S-shaped member.

5. The implant of claim 1 wherein, in a final state, the distal concave arm of the second S-shaped member opposes the proximal concave arm of the first S-shaped member.

6. The implant of claim 1 wherein at least one of the central elements has an upper surface adapted to bear upon an upper spinous process in an expanded state.

7. The implant of claim 1 wherein at least one of the central elements has a lower surface adapted to bear upon a lower spinous process in an expanded state.

8. The implant of claim 1 wherein the locking element is releasable.

9. The implant of claim 1 wherein the distal concave arm of the first S-shaped member lies in a first plane and the distal concave arm of the second S-shaped member lies in a second different plane.

10. The implant of claim 1 wherein at least one arm has a holding feature.

11. The implant of claim 1 wherein at least one central element has an anterior portion having a thickness and a posterior portion having a thickness, and wherein the thickness of the anterior portion is greater than the thickness of the posterior portion.

12. The implant of claim 1 wherein the distal concave arm of the first S-shaped member lies in a first plane and the proximal concave arm of the second S-shaped member lies in the first plane.

13. The implant of claim 1 wherein the distal concave arms are adapted to pass each other during pivoting.

14. An interspinous implant for insertion between adjacent spinous processes, the implant comprising:

a) a first S- shaped member having a central element, an upper arm attached to the central element and adapted to bear against the upper spinous process, and a lower arm attached to the central element and adapted to bear against the lower spinous process, and b) a second S-shaped member having a central element, an upper arm attached to the central element and adapted to bear against the upper spinous process, and a lower arm attached to the central element and adapted to bear against the lower spinous process and c) a pair of locking elements, each locking element comprising a pin having a leaf spring extending therefrom, wherein each locking element is received in a corresponding cavity in each of the central elements, wherein the central elements of the first and second members are pivotally connected.

15. The implant of claim 14 wherein at least one arm is concave.

16. The implant of claim 14 wherein each upper arm is concave.

17. The implant of claim 14 wherein each arm is concave.

18. The implant of claim 14 wherein at least one of the central elements has an upper surface adapted to bear upon an upper spinous process in a final state.

19. The implant of claim 14 wherein at least one of the central elements has a lower surface adapted to bear upon a lower spinous process in a final state.

20. The implant of claim 1, wherein, when the two S-shaped members are aligned in their final position, the cavities of the two central elements become aligned and the pin seated in the cavity pops up to become partially seated in the opposing cavity on central element, thereby locking the implant in its final position.

* * * * *

UNITED STATES PATENT AND TRADEMARK OFFICE

CERTIFICATE OF CORRECTION

PATENT NO. : 7,585,313 B2
APPLICATION NO. : 11/315660
DATED : September 8, 2009
INVENTOR(S) : Kwak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Fourteenth Day of September, 2010

David J. Kappos

*Director of the United States Patent and Trademark Office*